(12) United States Patent
Eckhardt et al.

(10) Patent No.: US 9,945,806 B2
(45) Date of Patent: *Apr. 17, 2018

(54) ELECTROCHEMICAL GAS SENSORS WITH IONIC LIQUID ELECTROLYTE SYSTEMS

(71) Applicant: MSA Europe GmbH, Jona (CH)

(72) Inventors: Rolf Eckhardt, Alzenau (DE); Martin Weber, Meckenheim (DE); Kathrin Keller, Konigswinter (DE); Kathrin Tölle, Konigswinter (DE); Ralf Warratz, Bonn (DE)

(73) Assignee: MSA EUROPE GMBH, Jona (CH)

( * ) Notice: Subject to any disclaimer, the term of this patent is extended or adjusted under 35 U.S.C. 154(b) by 307 days.

This patent is subject to a terminal disclaimer.

(21) Appl. No.: 14/743,045

(22) Filed: Jun. 18, 2015

(65) Prior Publication Data

US 2016/0011143 A1    Jan. 14, 2016

Related U.S. Application Data

(63) Continuation of application No. 13/131,324, filed as application No. PCT/EP2009/065806 on Nov. 25, 2009, now Pat. No. 9,063,079.

(51) Int. Cl.
*G01N 27/413* (2006.01)
*G01N 27/401* (2006.01)
*G01N 27/404* (2006.01)

(52) U.S. Cl.
CPC ......... *G01N 27/413* (2013.01); *G01N 27/401* (2013.01); *G01N 27/4045* (2013.01)

(58) Field of Classification Search
CPC . G01N 27/401; G01N 27/4045; G01N 27/413
See application file for complete search history.

(56) References Cited

U.S. PATENT DOCUMENTS

| | | | |
|---|---|---|---|
| 3,328,277 | A | 6/1967 | Solomons et al. |
| 3,824,168 | A | 7/1974 | Oswin et al. |
| 4,169,779 | A | 10/1979 | Tataria et al. |
| 4,474,648 | A | 10/1984 | Tantram et al. |
| 4,802,957 | A | 2/1989 | Kuwata et al. |
| 5,126,035 | A | 6/1992 | Kiesele et al. |
| 5,228,974 | A | 7/1993 | Kiesele et al. |
| 5,318,912 | A | 6/1994 | Silver et al. |
| 5,565,075 | A | 10/1996 | Davis et al. |
| 5,667,653 | A | 9/1997 | Schneider et al. |

(Continued)

FOREIGN PATENT DOCUMENTS

| | | |
|---|---|---|
| CN | 1640931 A | 7/2005 |
| DE | 2155935 | 6/1972 |

(Continued)

OTHER PUBLICATIONS

Compton et al. (J. Electroanal. Chem. 520, 2002, 71-78).*

(Continued)

*Primary Examiner* — Gurpreet Kaur
*Assistant Examiner* — Steven E Rosenwald
(74) *Attorney, Agent, or Firm* — The Webb Law Firm

(57) ABSTRACT

An electrochemical gas sensor includes an electrolyte including at least one ionic liquid which includes an additive portion including at least one organic additive, at least one organometallic additive or at least one inorganic additive.

19 Claims, 10 Drawing Sheets

(56) References Cited

U.S. PATENT DOCUMENTS

| | | |
|---|---|---|
| 5,855,809 A | 1/1999 | Angell et al. |
| 6,248,224 B1 | 6/2001 | Kitzelmann |
| 7,060,169 B2 | 6/2006 | Rohrl |
| 7,147,761 B2 | 12/2006 | Davis et al. |
| 7,217,354 B2 | 5/2007 | Mahurin et al. |
| 7,403,319 B2 | 7/2008 | Leyland et al. |
| 7,758,735 B2 | 7/2010 | Hengstenberg et al. |
| 8,540,899 B2 | 9/2013 | Miller |
| 2004/0033414 A1 | 2/2004 | Rohrl |
| 2006/0021873 A1 | 2/2006 | Mett |
| 2006/0237310 A1 | 10/2006 | Patel et al. |
| 2006/0278536 A1 | 12/2006 | Burrell et al. |
| 2007/0026295 A1 | 2/2007 | Angell et al. |
| 2007/0185330 A1 | 8/2007 | Walker |
| 2007/0231918 A1 | 10/2007 | Zeng |
| 2008/0035493 A1 | 2/2008 | Sommer et al. |
| 2008/0202930 A1 | 8/2008 | Mett |
| 2008/0209876 A1 * | 9/2008 | Miller ............... G11C 13/0009 55/522 |

FOREIGN PATENT DOCUMENTS

| | | | |
|---|---|---|---|
| DE | 4238337 C2 | 2/1994 | |
| DE | 69017039 T2 | 7/1995 | |
| DE | 19755506 C2 | 6/1999 | |
| DE | 19956302 C2 | 6/2001 | |
| DE | 102004037312 A1 | 3/2006 | |
| DE | 102005020719 B3 | 9/2006 | |
| DE | 102006014715 B3 | 6/2007 | |
| DE | 102006054948 A1 | 5/2008 | |
| DE | 102006054951 A1 | 5/2008 | |
| EP | 1600768 A1 | 11/2005 | |
| EP | 1384069 B1 | 6/2006 | |
| EP | 1722223 A1 | 11/2006 | |
| GB | 2225862 A | 6/1990 | |
| GB | 2332528 A | 6/1999 | |
| GB | 2395564 A | 5/2004 | |
| JP | 2003172722 A | 6/2003 | |
| JP | 2003172723 A | 6/2003 | |
| JP | 200517173 A | 1/2005 | |
| JP | 2005524825 A | 8/2005 | |
| JP | 200698269 A | 4/2006 | |
| JP | 2006156083 A | 6/2006 | |
| RU | 2141651 C1 | 11/1999 | |
| WO | 9718159 A1 | 5/1997 | |
| WO | 2008098137 A2 | 8/2008 | |
| WO | 2008110830 A1 | 9/2008 | |
| WO | WO 2008/110830 A1 * | 9/2008 | ........... G01N 27/416 |

OTHER PUBLICATIONS

Honeybourne et al. (J. Chem. Soc., Faraday Trans. 1, 1984, 80, 851-863).*

Buzzeo et al., "Non-Haloaluminate Room-Temperature Ionic Liquids in Electrochemistry—A Review," ChemPhysChem, 2004, pp. 1106-1120.

Cai et al., "Studies on a Sulfur Dioxide Electrochemical Sensor with Ionic Liquid as Electrolyte," Journal of East China Normal University, 2001, 7 pages.

Compton et al., "Direct electrochemical reduction of hemin in imidazolium-based ionic liquids," Journal of Electroanalytical Chemistry, 2002, pp. 71-78, vol. 520.

Earle and Seddon, "Ionic liquids. Green solvents for the future," Pure Appl. Chem., 2000, pp. 1391-1398, vol. 72, No. 7.

Honeybourne et al., "Use of Thin Films of Conjugated Organic Macrocycles as the Active Elements in Toxic-gas Sensors Operating at Room Temperature," J. Chem. So., 1984, pp. 851-863, vol. 80.

Silvester et al., "Electrochemistry in Room Temperature Ionic Liquids: A Review and Some Possible Applications," Z. Phys. Chem., 2006, pp. 1247-1274, vol. 220.

Wacker Chemie AG: Da Steckt mehr drin als man denkt: HDK—Pyrogene Kieselsaure, Munchen, 2005.

Wasserscheid et al., "Ionic Liquids—New 'Solutions' for Transition Metal Catalysis," Angew. Chem. Int. Ed., 2000, pp. 3772-3789, vol. 39.

Wei et al., "Applications of ionic liquids in electrochemical sensors," Analytica Chimica Acta, 2008, pp. 126-135, vol. 607.

* cited by examiner

ELECTROCHEMICAL GAS SENSORS WITH IONIC LIQUID ELECTROLYTE SYSTEMS

CROSS-REFERENCE TO RELATED APPLICATION

This application claims priority to U.S. application Ser. No. 13/131,324 filed on Nov. 25, 2009, the disclosure of which is hereby incorporated in its entirety by reference. Also, this application claims the benefit of German Patent Application Nos. 10 2008 044 238.0 and 10 2008 044 239.9, each filed Dec. 1, 2008, the disclosures of which are incorporated herein by reference.

BACKGROUND

The basic measuring component of a gas sensor is an electrochemical cell, which includes at least two electrodes in contact with one another via an electrolyte (that is, an ionic conductor). On the side of the cell which is open to the atmosphere, analyte gas can flow to one of the electrodes (the working or sensing electrode) at which it is electrochemically converted. The current generated from the conversion is proportional to the quantity of gas present. A signal, which can, for example, be used to provide an alarm, is generated from the current. A variety of electrolyte systems are described in the literature. Sulfuric acid is one of the most commonly used electrolytes, and is used in sensors for common gases, such as, for example, CO, $H_2S$ or $O_2$. See, for example, U.S. Pat. No. 3,328,277.

Aqueous electrolytes including a neutral or a basic inorganic salt as a conducting salt have also been described for use in connection with analyte gases sufficiently reactive only in neutral electrochemical media. See, for example, U.S. Pat. No. 4,474,648 and German Patent No. DE 4238337.

The electrolyte systems described above are hygroscopic (that is, they can absorb water from the surrounding environment). A hydroscopic electrolyte can be desirable for use in dry or low-humidity environments to delay drying of the cell. In high-humidity environments, however, a hydroscopic electrolyte can absorb so much water that electrolyte leaks from the sensor cell. To prevent leakage of electrolyte, a sensor cell typically includes extra or reserve volume of approximately five to seven times its electrolyte fill volume. Inclusion of such a substantial reserve volume cuts against a general aim of reducing the overall size of sensor cells.

In a number of sensors, organic liquids, which include conducting salts admixed therein to ensure ionic conductivity, are used as electrolytes to limit water absorption in high-humidity environments. See, for example, U.S. Pat. No. 4,169,779. The advantage at high relative humidity, however, becomes a disadvantage at low humidity and/or high ambient temperature, as vaporized solvent cannot be reabsorbed from the atmosphere and is thus irrecoverably lost from the sensor cell.

Ionic liquids (IL) have also been used as electrolytes. Ionic liquids are defined as liquid salts with a melting point below 100° C. The salt-like structure of ionic liquids can result in the absence of a measurable vapor pressure. The properties of ionic liquids vary substantially and are dependent, for example, upon the type and the number of organic side chains present in the ionic liquid, as well as the anions and cations therein. Ionic liquids are available having melting points below −40° C. Many ionic liquids are both chemically and electrochemically stable and have a high ionic conductivity. A number of ionic liquids are not measurably hygroscopic. Such properties make ionic liquids good electrolytes in electrochemical gas sensors.

The use of ionic liquids in gas sensors was first described for use in connection with high sulfur dioxide concentrations. Cai at al., Journal of East China Normal University (Natural Science), article number 1000-5641(2001)03-0057-04. The use of ionic liquids as electrolytes in gas sensors is also disclosed, for example, in Great Britain Patent No. GB 2395564, U.S. Pat. No. 7,060,169 and published German patent application DE 102005020719. GB 2395564 describes generally the use of Ionic liquids as electrolytes. U.S. Pat. No. 7,060,169 discloses the use of pure imidazolium and pyridinium salts as ionic liquid electrolytes. Published German patent application DE 102005020719 discloses the possibility of forming an open gas sensor without a diffusion membrane. The potential for the use of such technology in miniaturizing sensors is described in published German patent application DE 102004037312.

Although ionic liquids are used in a number of gas sensors as a replacement for classic (aqueous) electrolytes, little or no consideration is given to the fact that classic (aqueous) sensor systems often go through secondary reactions to increase their sensitivity or selectivity to a particular analyte. Examples of this effect can be found, for example, in European Patent EP 1 600 768, U.S. Pat. No. 6,248,224 and published German patent application DE 102006014715.

The chemical processes in ionic liquids differ fundamentally from those in aqueous and organic systems, and chemical processes in ionic liquids are not well characterized. See, for example, P. Wasserscheid, Angew. Chem. 2000, 112, 3926-3945 and K. R. Seddon, Pure Appl. Chem. Vol. 72, No. 7, pp. 1391-1398, 2000.

Position or orientation independence of sensor performance is also important for an electrochemical gas sensor. Immobilizing liquid electrolytes using glass fibers or silicate structures to form a quasi-solid electrolyte improves position independence. With a quasi-solid electrolyte, reaction products and electrolytes are prevented from migrating through the sensor and cannot deposit on sensitive sites (for example, upon the working electrode or the reference electrode). Furthermore, there is no depletion as a result of leaching processes between the electrodes, which facilitates miniaturization of the sensor cells. Quasi-solid electrolyte systems formed with conventional electrolyte liquids are, for example, disclosed in U.S. Pat. Nos. 7,145,561, 7,147,761, 5,565,075 and 5,667,653. The systems described therein, provide improved response time and allow for a compact design, but exhibit disadvantages associated with conventional, hygroscopic electrolytes.

Advantages of using a quasi-solid electrolyte with ionic liquid electrolytes are discussed in Published PCT International Patent Application WO 2008/110830, which discloses an electrochemical sensor having an ionic liquid immobilized in a support material. A number of anions and cations are described for the ionic liquid. The cations disclosed include imidazolium, pyridinium, tetraalkylammonium, and tetraalkylphosphonium cations. The sensor of Published PCT International Patent Application WO 2008/110830 is used for the detection of gases in the air exhaled by a patient to, for example, enable diagnosis of asthma. That sensor is operated in a cyclic voltammetric mode. In cyclic voltammetry, the potential of the working electrode is varied between preset potential limits at a constant rate.

Reducing agents such as quinones and quinolines are added to the electrolyte of Published PCT International Patent Application 2008/110830. Because the measurement in that sensor occurs by cyclic voltammetry, the electrochemical reduction of the analyte(s) at the electrodes is improved. To obtain acceptable solubility, additional co-solvents have to be used when adding the reducing agents. In addition, redox catalysts can be added. Because of the cyclovoltammographic operating mode, the sensor of Published PCT International Patent Application 2008/110830 is not suitable for continuous monitoring of a gas mixture. The sensor of Published PCT International Patent Application 2008/110830 is suitable only for limited duration measurements of gas mixtures in which the composition varies little.

SUMMARY

In one aspect, an electrochemical gas sensor includes an electrolyte including at least one ionic liquid which includes an additive portion including at least one organic additive, at least one organometallic additive or at least one inorganic additive.

The sensor can, for example, include at least two electrodes in electrical contact with the ionic liquid, wherein the electrodes are separated from one another by a separator or by space.

The electrodes can, for example, include (independently, the same or different) a metal selected from the group of Cu, Ni, Ti, Pt, Ir, Au, Pd, Ag, Ru, Rh, an oxide of Cu, Ni, Ti, Pt, Ir, Au, Pd, Ag, Ru, or Rh, a mixture of such metals and/or metal oxides, or carbon.

The additive portion can, for example, be present in an amount of 0.05 to 15 weight %. One or more organic additives, when present, can, for example, be present in an amount of 0.05 to 5.0 weight %. More particularly, one or more organic additives, when present, can, for example, be present in an amount of 0.05 to 1.5 weight %. One or more inorganic additives, when present, can, for example, be present in an amount of 1 to 12 weight %. One or more organometallic additives, when present, can, for example, be present in an amount of 0.05 to 5.0 weight %. More particularly, one or more organometallic additives, when present, can, for example, be present in an amount of 0.05 to 1 weight %.

The ionic liquid can, for example, include at least one cation which is selected from the group of imidazolium, pyridinium, guanidinium, the cation being unsubstituted or substituted with at least one of an aryl group or a C1 to C4 alkyl group, the aryl group and the C1 to C4 alkyl group being unsubstituted or substituted with at least one of a halogen, a C1 to C4 alkyl group, a hydroxyl group or an amino group.

In several embodiments, the ionic liquid includes at least one of an imidazolium cation, a C1 to C4 alkyl imidazolium cation, a pyridinium cation or a C1 to C4 alkyl pyridinium cation.

The ionic liquid can, for example, include at least one anion selected from the group of the a halide anion, a nitrate anion, a nitrite anion, a tetrafluoroborate anion, a hexafluorophosphate anion, a polyfluoroalkane sulphonate anion, a bis(trifluoromethylsulfonyl)imide anion, an alkyl sulphate anion, an alkane sulphonate anion, an acetate anion and an anion of a fluoroalkane acid.

In several embodiments, the ionic liquid includes at least one anion selected from the group of a C1-C6 alkyl sulphate anion and a C1-C6 alkane sulphonate anion. The ionic liquid can, for example, include at least one anion from the group of a methyl sulphate anion, an ethyl sulphate anion, a butyl sulphate anion, a methanesulphonate anion, an ethanesulphonate anion and a butanesulphonate anion.

In several embodiments, the ionic liquid includes 1-ethyl-3-methylimidazolium methanesulphonate.

In a number of embodiments, the at least one organic additive is imidazole, a C1 to C4 alkyl imidazole, pyridine, a C1 to C4 alkyl pyridine, pyrrole, a C1 to C4 alkyl pyrrole, pyrazole, a C1 to C4 alkyl pyrazole, pyrimidine, a C1 to C4 alkyl pyrimidine, guanine, a C1 to C4 alkyl guanine, uric acid, benzoic acid, a porphyrin, or a porphyrin derivative.

In a number of embodiments, the at least one organic additive is selected from the group of imidazole, a C1 to C4 alkyl imidazole, pyrimidine or a C1 to C4 alkyl pyrimidine.

In a number of embodiments, the at least one organometallic additive is selected from the group of organometallic porphyrins and organometallic porphyrin derivatives. The organometallic porphyrin can, for example, be selected from the group of porphyrins with at least one meso-alkyl substituent, at least one β-alkyl substituent, at least one aryl substituent, and their derivatives. In a number of embodiments, the organometallic porphyrin is a metal phthalocyanine with $Mn^{2+}$, $Cu^{2+}$, $Fe^{2+/3+}$ or $Pb^{2+}$ as the metal cation.

In several embodiments, the at least one inorganic additive is selected from the group of an alkali halide, an ammonium halide, a C1 to C4 alkyl ammonium halide, a transition metal salt and a lead salt. The transition metal salt can, for example, be a salt of $Mn^{2+}$, $Cu^{2+}$ $Ag^+$, $Cr^{3+}$, $Cr^{6+}$, $Fe^{2+}$, or $Fe^{3+}$ and the lead salt can be a salt of $Pb^{2+}$.

In several embodiments, the at least one inorganic additive is selected from the group of lithium bromide, lithium iodide, ammonium iodide, tetramethylammonium iodide, tetraethylammonium iodide, tetrapropylammonium iodide, tetrabutylammonium iodide, tetrabutylammonium bromide, manganese(II) chloride, manganese(II) sulphate, manganese(II) nitrate, chrom(III) chloride, alkali chromates, iron(II) chloride, iron(III) chloride and lead(II) nitrate.

The electrolyte can, for example, be substantially absorbed in a solid material.

At least a part of the additive portion can, for example, be immobilized upon a solid support. At least a part of the additive portion can, for example, be immobilized upon the solid material. At least a part of the additive portion can, for example, be immobilized upon at least one of the electrodes.

In another aspect, an electrochemical gas sensor as described above is used for the detection/measurement of gases selected from the group of acid gases, basic gases, neutral gases, oxidizing gases, reducing gases, halogen gases, halogen vapours, and hydride gases.

In another aspect, an electrochemical gas sensor as described above is used for the detection/measurement of gases selected from the group of $F_2$, $Cl_2$, $Br_2$, $I_2$, $O_2$, $O_3$, $ClO_2$, $NH_3$, $SO_2$, $H_2S$, CO, $CO_2$, NO, $NO_2$, $H_2$, HCl, HBr, HF, HCN, $PH_3$, $AsH_3$, $B_2H_6$, $GeH_4$ and $SiH_4$.

In a further aspect, an electrochemical gas sensor as described above is used for the detection/measurement of gases selected from the group of $NH_3$, $SO_2$, $H_2S$, $H_2$, HCl, HCN and hydride gases, wherein the ionic liquid comprises at least one organic additive.

In another aspect, an electrochemical gas sensor is used for the detection/measurement of gases from the group of $NH_3$, $SO_2$ $H_2S$, wherein the ionic liquid includes at least one organic additive selected from the group of imidazole, a C1 to C4 alkyl imidazole, pyridine, a C1 to C4 alkyl pyridine, pyrrole, a C1 to C4 alkyl pyrrole, pyrazole, a C1 to C4 alkyl pyrazole, pyrimidine, a C1 to C4 alkyl pyrimidine, guanine, a C1 to C4 alkyl guanine, uric acid, benzoic acid, a porphyrin and a porphyrin derivative.

In a number of embodiments, the electrochemical gas sensor can, for example, be for the detection/measurement of gases selected from the group of $NH_3$, $SO_2$ $H_2S$, wherein the ionic liquid comprises at least one organic additive selected from the group of imidazole, a C1 to C4 alkyl imidazole, pyrimidine, and a C1 to C4 alkyl pyrimidine.

In several embodiments, the electrochemical gas sensor can, for example, be used for the detection/measurement of gases selected from the group of $F_2$, $Cl_2$, $Br_2$, $I_2$, $O_3$, $ClO_2$, $NH_3$, $H_2$, HCl, HCN and a hydride gas, wherein the ionic liquid comprises at least one inorganic additive.

In a number of embodiments, the electrochemical gas sensor can, for example, be for the detection/measurement of gases selected from the group of $Cl_2$, $Br_2$, $O_3$, $ClO_2$ and $NH_3$, wherein the ionic liquid includes at least one inorganic additive selected from the group of an alkali halide, an ammonium halide, and a C1 to C4 alkyl ammonium halide, a transition metal salt of $Mn^{2+}$, $Mn^{3+}$, $Cu^{2+}$, $Ag^+$, $Cr^{3+}$, $Cr^{6+}$, $Fe^{2+}$, $Fe^{3+}$ and a lead salt of $Pb^{2+}$.

In several embodiments, the electrochemical gas sensor can, for example, be used for the detection/measurement of gases selected from the group of $Cl_2$, $Br_2$, $O_3$, $ClO_2$ and $NH_3$, wherein the ionic liquid includes at least one inorganic additive selected from the group of lithium bromide, lithium iodide, tetrabutylammonium iodide, tetrabutylammonium bromide, manganese(II) chloride, manganese(II) sulphate and manganese(II) nitrate, chrom(III) chloride, alkali chromates, iron(II) chloride, iron(III) chloride and lead(II) nitrate.

In a number of embodiments, the electrochemical gas sensor can, for example, be for the detection/measurement of gases selected from the group of CO, $O_2$, NO, $NO_2$ and $H_2$, wherein the ionic liquid comprises at least one organometallic additive. The ionic liquid can, for example, include at least one organometallic additive selected from the group of an organometallic porphyrin and an organometallic porphyrin derivative.

In several embodiments, the electrochemical gas sensor is used for the detection/measurement of gases selected from the group of CO, NO, $NO_2$ and $H_2$, wherein the ionic liquid includes at least one organometallic additive selected from the group of a metal phthalocyanine with $Mn^{2+}$ $Cu^{2+}$ $Fe^{2+/3+}$ or $Pb^{2+}$ as the metal cation.

In another aspect, an electrochemical gas sensor includes a housing including at least one inlet, at least two electrodes in the housing, and an electrolyte in contact with the at least two electrodes. The electrolyte includes an ionically conductive liquid and an additive portion including at least one organic additive, at least one organometallic additive or at least one inorganic additive, and the electrolyte is substantially absorbed in a solid material. In several embodiments, the solid material can, for example, be a powdered silicate having an average particle size of at least 5 µm, a specific surface area of at least 50 $m^2/g$, and a $SiO_2$ content of at least 95% by weight. The powdered silicate can, for example, have an average particle size of 100 µm, a specific surface area of 190 $m^2/g$, and a $SiO_2$ content of at least 98% by weight. In several other embodiments, the solid material is a fibrous nonwoven glass fiber.

The solid material can, for example, be present in the sensor as a bed, in a layered arrangement or in compressed form.

Solid materials can, for example, present in the sensor in compressed form with the at least two electrodes pressed therein.

The performance of gas sensors hereof with regard to, for example, sensitivity, response time, selectivity and/or robustness is improved using an ionic liquid as electrolyte wherein the ionic liquid includes additives such as at least one organic compound, at least one organometallic compound and/or at least one inorganic compound as compared to pure ionic liquids or mixtures thereof.

The compositions, devices, systems, uses and/or methods described herein, along with the attributes and attendant advantages thereof, will best be appreciated and understood in view of the following detailed description taken in conjunction with the accompanying drawings.

DETAILED DESCRIPTION

Figure 1A:
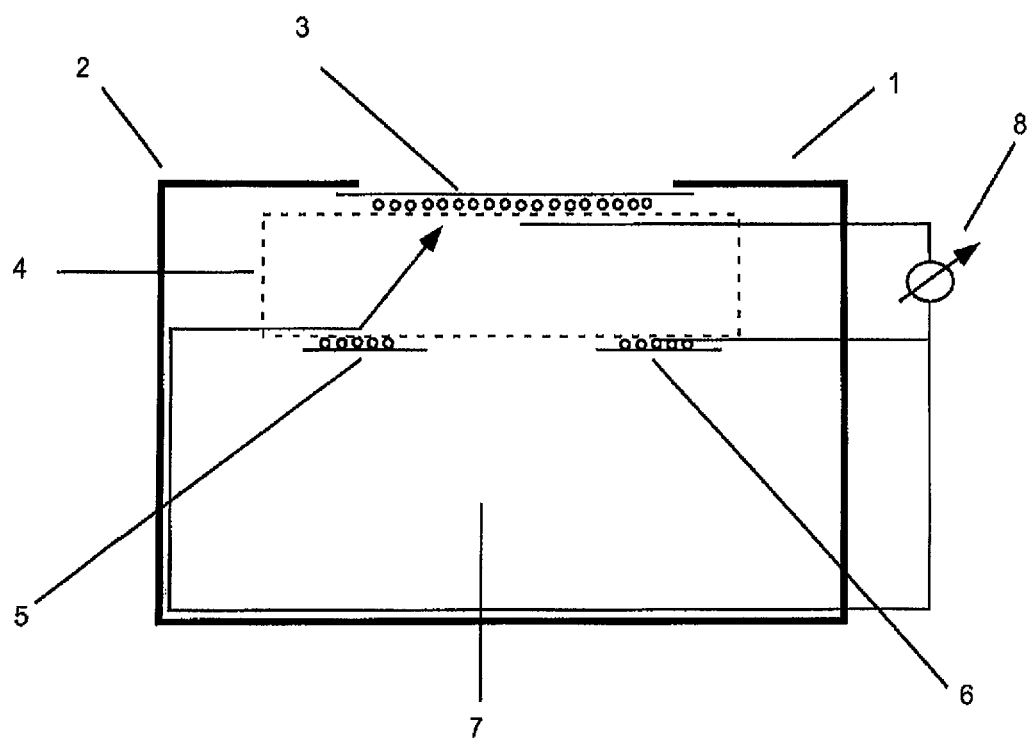
FIG. 1A illustrates a schematic representation of a three-electrode electrochemical gas sensor.

As used herein and in the appended claims, the singular forms "a," "an", and "the" include plural references unless the content clearly dictates otherwise. Thus, for example, reference to "an additive" includes a plurality of such additives and equivalents thereof known to those skilled in the art, and so forth, and reference to "the additive" is a reference to one or more such additives and equivalents thereof known to those skilled in the art, and so forth.

In a number of representative embodiments, the electrochemical gas sensor includes at least two electrodes which are in contact with an ionic liquid electrolyte (which can include one or more ionic liquids) and which are electrically isolated from one another (for example, by one or more separators or by space). As described above, ionic liquids are defined as liquid salts with a melting point below 100° C. In a number of embodiments, the ionic liquids of the sensors hereof are liquids under ambient conditions (for example, at room temperature or approximately 25° C.)

The ionic liquid electrolyte includes an additive portion including at least one of an organic additive (for example, an compound), an organometallic additive (for example, an organometallic compound) or an inorganic additive (for example, an inorganic compound). In general, the organic additive, the organometallic additive and/or the inorganic additive are not ionic liquids.

Sensors including two, three or four and more electrodes are possible. In several embodiments, the sensors include two electrodes or three electrodes. In several representative embodiments studied, the sensor includes a housing. The housing includes at least one opening through which the gas to be detected enters into the sensor. In another embodiment electrodes can be printed upon a printed circuit board or upon flexible materials (for example, upon fabrics).

In several representative embodiments, a liquid electrolyte including at least one ionic liquid is substantially absorbed in a solid material (for example, a powdered solid material and/or fibrous nonwoven solid material, which can, for example, be formed at least partially from $SiO_2$). The absorbed ionically conductive liquid can include an additive portion as described above. As used herein in connection with an ionic liquid absorbed in a solid material, the term "substantially" indicated that the electrolyte is absorbed to an extent of at least 90%. The electrolyte can also be to an extent of at least 95%, or even at least 99%.

In a number of embodiments, an additive or additives as described above is/are mixed with the ionic liquid electrolyte and can be at least partially solubilized therein and/or at least partially suspended therein. In other embodiments, the additives can be immobilized upon a solid support or otherwise incorporated in, or form a part of, a solid support and placed in contact with the ionic liquid electrolyte. As used herein, the term "immobilized" refers to entities that are attached to a separate solid support, as well as to entities that form a portion or all of a solid support.

An additive can, for example, be immobilized upon a solid support by reacting the additive or a precursor thereof (for example, to form a covalent bond or an ionic bond) with a solid support such that the additive or an active residue of the additive is immobilized upon or within the solid support. An additive or a precursor thereof can also be immobilized upon a support by absorption, adsorption, chelation, hydrogen bonding, entrapment and/or other techniques known for immobilization of chemical entities. The method of immobilization should leave the immobilized additive or additives available for interaction with, for example, the electrolyte, the analyte and/or other entities.

An immobilized additive can, for example, be placed in close proximity to a specific area (for example, an inlet of the sensor, the working electrode and/or other electrode) to improve the efficacy of the immobilized additive (for example, via interaction or reaction with the analyte gas or another entity). A plurality of solid supports can be used to immobilize an additive or additives. An additive or additive can be immobilized upon or within a porous matrix. In a number of embodiments, an additive or additives is/are immobilized upon a solid material within or upon which the electrolyte is absorbed as described herein. An additive or additives can also or alternatively be immobilized upon the working electrode and/or other electrode.

As described above, the electrochemical gas sensors can, for example, be two-, three-, or multi-electrode systems. In a two-electrode system includes one working electrode (WE) and one counter electrode (CE). A three-electrode system further includes a reference electrode (RE). Multi-electrodes systems can be equipped with a protective electrode or further working electrodes. In a number of representative studies, the potential of the working electrode was maintained to be generally constant. However, the potential of the working electrode can also be varied.

The electrodes can, for example, include an electrocatalytic metal from the group of Cu, Ni, Ti, Pt, Ir, Au, Pd, Ag, Ru, Rh, oxides thereof, mixtures of such metals or metal oxides, or carbon. The materials of the individual electrodes of the sensors can be identical or different. The electrodes can have any suitable shape. In a number of embodiments, the electrode material(s) are applied to a membrane permeable to gases. Electrocatalyst material(s) can also, for example, be directly mixed in the form of a powder with an electrolyte that is, with absorbed ionic liquid (with or without additive(s)). In the second case, care must be taken that absorbed electrolyte powder is present between the electrode material powders to prevent a short circuit between the electrodes.

The sensor housing can, for example, be formed of a metal or any other suitable material. Because ionic liquids, in contrast to conventional electrolytes such as sulfuric acid, are not highly corrosive, there are few if any problems with regard to corrosion of metallic housings. Polymers or plastics are also examples of suitable materials for the housing.

In the case that the electrolyte is absorbed upon a powdered solid material, the powdered solid can, for example, be a silicate having an average particle size of at least 5 μm, at least 50 μm, or at least 75 μm; having a specific surface area of at least 50 $m^2/g$, at least 100 $m^2/g$, or at least 150 $m^2/g$; and a $SiO_2$ content of at least 95% by weight. The term "silicate" includes variants of $SiO_2$ such as silica gels and silicates (for example SIPERNAT® silica particles and SIDENT® silica, available from Evonik Degussa GMBH of Essen, Germany). In several embodiments, the silicate is pure $SiO_2$, alumosilicates or calcium silicates. The specific surface area can vary widely. For example, a specific surface area in the range of 50 $m^2/g$ to 500 $m^2/g$ is suitable. In several embodiments, a silicate having an average particle size of 100 μm, a specific surface area of 190 $m^2/g$, and a $SiO_2$ content of at least 98% by weight was used as a solid support for the liquid electrolyte.

In other embodiments of sensors including an absorbed electrolyte, the liquid electrolyte was absorbed upon a fibrous nonwoven solid material (for example, $SiO_2$) in the form of a glass fiber.

The solid material (in which the liquid electrolyte is substantially absorbed) can be present within the sensor as bed, in a layered arrangement or in compressed form. The bed or layered arrangement provides for a flexibility in the design of the sensors. Compression can take place in several steps. Compression to form a pellet provides advantages in production. The sensor can be assembled so that the pellet can be positioned between two electrodes. The entire assembly can be compressed by the sensor housing.

Electrodes can be compressed together with compressed $SiO_2$ before being placed within the sensor to reduce assembly steps. Contact between the electrodes and electrolyte can also be improved via such compression, which has a positive effect on the sensitivity and response time of the sensor.

The ratio of electrolyte to the $SiO_2$ material can vary over a wide range. A ratio of electrolyte to solid $SiO_2$ material in the range of one to two parts to one to one part by weight is, for example, suitable. Even in the case of excess electrolyte, a substantially dry powder is still achieved (that is, the electrolyte is "substantially" absorbed to at least 90%, to at least 95%, and even to at least 99%). The resultant pellet can, for example, have a weight of approximately 200 mg, in which ½ to ⅔ of the weight is electrolyte and ½ to ⅓ of the weight is the solid material.

Sensor designs incorporating a quasi-solid electrolyte suitable for use in the present sensor are disclosed in U.S.

Pat. Nos. 7,145,561, 5,565,075, 7,147,761, and 5,667,653. The design and material of the housing as well as the arrangement and design of the quasi-solid electrolyte of those references can be incorporated herein.

An additive or additives can, for example, be included within the electrolyte in an amount of 0.05 to 15 weight-%.

Organic additives can, for example, be included in an amount of 0.05 to 5.0 weight-%. More particularly, organic additives can, for example, be included in an amount of 0.05 to 1.5 weight-%. Inorganic additives can, for example, be included in an amount of 1 to 12 weight-%. Organometallic additives can, for example, be included in an amount of 0.05 to 5.0 weight-%. More particularly, organometallic additives can, for example, be included in an amount of 0.05 to 1 weight-%.

The performance of gas sensors can be improved significantly with regard to, for example, sensitivity, response time, selectivity and robustness, by adding such additives to an ionic liquid in forming an electrolyte.

The ionic liquid can include at least one cation which is selected from the group of an imidazolium cation, a pyridinium cation, and a guanidinium cation. These cations can be unsubstituted or substituted with at least one aryl group and/or at least one C1 to C4 alkyl group, The aryl and/or the alkyl group substituent can itself be unsubstituted or substituted with at least one of a halogen, a C1 to C4 alkyl group, a hydroxyl group or an amino group. In several embodiments, the ionic liquid includes at least one of an imidazolium cation or a pyridinium cation, which cations can be unsubstituted or substituted with at least one C1 to C4 alkyl group.

The ionic liquid can, for example, include at least one anion from the group of the a halide anion (that is, chloride, iodide, bromide or fluoride), a nitrate anion, a nitrite anion, a tetrafluoroborate anion, a hexafluorophosphate anion, a polyfluoroalkane sulphonate anion, a bis(trifluoromethylsulfonyl)imide anion, an alkyl sulphate anion, an alkane sulphonate anion, acetates and an anion of a fluoroalkane acid.

The at least one anion can, for example, be an anion from the group of a C1-C6 alkyl sulphate anion and a C1-C6 alkane sulphonate anion. In a number of embodiments, the ionic liquid includes at least one anion from the group a methyl sulphate anion, an ethyl sulphate anion, a butyl sulphate anion, a methanesulphonate anion, an ethanesulphonate anion and a butanesulphonate anion.

In several embodiments, the ionic liquid is 1-ethyl-3-methylimidazolium methanesulphonate.

A mixture of various ionic liquids can be used to, for example, provide for different polarities in the electrolyte. Adjusting polarity can help to dissolve certain additives, and can also assist in controlling water absorption of the electrolyte. The hydrophilicity of the electrolyte influences the three phase limit on the sensing electrode (SE).

Mixtures of various additives can also be used in the electrolyte. The additive mixture can be a mixture of various additives of the same group (for example, a mixture of various organic additives). The mixture of different additives can also include additives from different groups (for example, a mixture of organic and inorganic additives). The cross-sensitivity pattern of sensors can, for example, be adapted to specific requirements by using mixtures of various additives.

The electrochemical gas sensors can, for example, be used for the detection/measurement of an acidic gas, a basic gas, a neutral gas, an oxidizing gas, a reducing gas, a halogen gas and/or vapors, and a hydride gases. For example, the sensors can be used for the detection/measurement of $F_2$, $Cl_2$, $Br_2$, $I_2$, $O_2$, $O_3$, $ClO_2$, $NH_3$, $SO_2$, $H_2S$, $CO$, $CO_2$, $NO$, $NO_2$, $H_2$, $HCl$, $HBr$, $HF$, $HCN$, $PH_3$, $AsH_3$, $B_2H_6$, $GeH_4$ or $SiH_4$.

It is believed that the action of organic additives is based on stabilization of the reference potential, as well as the pH value. Such stabilization is particularly advantageous for acid gas analytes.

The at least one organic additive can, for example, be selected from the group of imidazole, pyridine, pyrrole, pyrazole, pyrimidine, guanine (each of which can be unsubstituted or substituted with at least one C1 to C4 alkyl group), uric acid, benzoic acid, a porphyrin, or a derivative of a porphyrin. In a number of embodiments, the at least one organic additive is selected from the group of imidazole or pyrimidine, which organic additives can be unsubstituted or substituted with at least one C1 to C4 alkyl group.

An electrochemical gas sensor in which the ionic liquid electrolyte includes at least one organic additive can, for example, be used for the detection/measurement of $NH_3$, $SO_2$, $H_2S$, $H_2$, $HCl$, $HCN$ or a hydride gas. In several embodiments of a sensor for the detection/measurement of $NH_3$, $SO_2$, or $H_2S$, the ionic liquid electrolyte includes at least one organic additive from the group of imidazole, pyridine, pyrrole, pyrazole, pyrimidine, guanine (each of which can be unsubstituted or substituted with at least one C1 to C4 alkyl group), uric acid, benzoic acid, a porphyrin, and a derivative of a porphyrin. In a number of embodiments, the electrochemical gas sensor is used for the detection/measurement of $NH_3$, $SO_2$, or $H_2S$, and the ionic liquid includes at least one organic additive selected from the group of imidazole and pyrimidine (each which can be unsubstituted or substituted with at least one C1 to C4 alkyl group).

The addition of 0.1 to 15% of organic bases such as, for example, imidazole, pyridine or guanine derivatives approximately doubles the sensitivity of sensors to acidic gases such as, for example, hydrogen sulfide or sulfur dioxide. The sensors also operate in a significantly more stable manner when subjected to these gases. This result is unexpected when one considers that all commercially available sensors for such gases use acidic electrolytes such as, for example, sulfuric acid. The effect of the additives are believed to rest on two principles. First, one can observe a marked shift in the reference potential when compared with electrolytes without additives, which presumably leads to the stabilizing of the signal. Second, the basic system seems to act as a buffer and to prevent acid gases from dissolving in the electrolyte, which would generate a shift in the reference potential by changing the pH.

The electrolyte solutions function as ionic conductors in gas sensors in the classic sense of a Clark cell (see, for example, FIG. 1A) with, for example, noble metal catalysts or carbon as electrode materials in two-, three-, and/or multi-electrode sensor systems.

Organic additives can be added to ionic liquids in the form of an aqueous solution or melted together with them. The manner of addition depends on the water solubility of the additive as well as on the hydrophilicity of the ionic liquid.

If one compares the effect of additives on the potentials which are measured between the sensing electrode (SE) and the reference electrode (RE) of the gas sensors with the effect on the sensor performance, differences result as a function of the gas being measured. As an example, a sensor cell was selected for study that reacted to both sulfur dioxide and chlorine (see Table 1).

TABLE 1

| to $SO_2$ | Potentials [mV] (average values) | |
|---|---|---|
| | SE vs RE | S [nA/ppm] (average values) |
| EMIM MeSO3 | −93 | 2070 |
| EMIM MeSO3 + imidazole | −144 | 2890 |
| EMIM MeSO3 + uric acid | −182 | 2000 |

In the case of the reaction to $SO_2$, the addition of imidazole and the addition of uric acid lead to the sensor potential between the sensing and the reference electrode becoming more negative. The size of the reference potential does not appear to be solely responsible for the increase in the sensitivity of $SO_2$ sensors. In both cases, however, the addition leads to a stabilization of the sensor signal (see FIGS. 2 and 3).

The sensors were also studied over a longer period of time. Even during the maturation period of the sensors in the first two weeks of use thereof, sensors with imidazole as an additive are significantly more sensitive than control sensors without an additive. This effect continues until the end of the observation period (see FIG. 4). Furthermore, the sensor curves progress steadily (that is, the curves do not collapse during the gas exposure).

The at least one organometallic additive can, for example, be selected from the group of the organometallic porphyrins and their derivatives. The organometallic porphyrins can, for example, be selected from the group of the porphyrins with at least one meso-alkyl, β-alkyl or aryl substituent, and derivatives thereof. Organometallic porphyrin derivatives can, for example, be selected from the group of metal phthalocyanines with $Mn^{2+}$, $Cu^{2+}$, $Fe^{2+/3+}$ or $Pb^{2+}$ as the metal cation.

An electrochemical gas sensor in which an ionic liquid electrolyte includes an organometallic additive can, for example, be used for the detection/measurement of CO, $O_2$, NO, $NO_2$ or $H_2$. Sensors for the detection/measurement of CO, $O_2$, NO, $NO_2$ or $H_2$ can, for example, include an ionic liquid electrolyte including at least one organometallic additive from the group of organometallic porphyrins and their derivatives.

In several embodiments of electrochemical gas sensors in which an ionic liquid electrolyte includes at least one organometallic additive, the gas sensor is used for the detection/measurement of CO, NO, $NO_2$ or $H_2$, and the ionic liquid includes at least one organometallic additive selected from the group of metal phthalocyanines with $Mn^{2+}$, $Cu^{2+}$, $Fe^{2+/3+}$ or $Pb^{2+}$ as the metal cation.

The selectivity of the sensors to certain gases (for example, carbon monoxide) can be significantly increased with the addition of metal porphyrin derivatives. Previously, this effect has been observed only in the case of semiconductor gas sensors. German Patent DE 19956302 describes a semiconductor gas sensor which is doped with various phthalocyanine derivatives. Upon exposure of that sensor to NO or $NO_2$ gas, a clearly lowered electron escape energy can be observed in the semiconductor material (which results, by way of a significant increase in the conductivity at the sensing electrode, to a sensor signal).

The increase in the sensitivity of the sensors described herein cannot be explained by an increase in conductivity, as the electrodes include graphite or noble metal and not an oxidic semiconductor.

A known problem in the field of electrochemical gas sensors is, for example, the strong cross-sensitivity of sensors with platinum electrodes to CO. As hydrogen sensors are also operated with platinum electrodes, it is not possible in classic sensor technology to sense hydrogen in the presence of carbon monoxide. The use of metal porphyrins in ionic liquid electrolytes can help to increase the selectivity of a sensor as the specific solubility of gases in ionic liquids is increased.

Ionic liquids including at least one organometallic additive function as ionic conductors or electrolytes in gas sensors in the classic sense of a Clark cell, as described above. Noble metal catalysts or carbon can be use in the sensing electrode (SE) and counter electrode (CE) as a two electrode system or with an additional reference electrode (RE) in a three-electrode system (or with additional electrodes if the sensor is, for example, equipped with a protective electrode or further sensing electrodes). Organometallic additives can be added to ionic liquids in the form of an aqueous solution, can be melted together with ionic liquids or can be suspended in ionic liquids. The manner of addition depends on the water solubility of the additive, the hydrophilicity of the ionic liquid and any secondary reactions.

With regard to electrochemical gas sensors in which an ionic liquid electrolyte includes at least one inorganic additive, the inorganic additive can, for example, be selected from the group of an alkali halide, an ammonium halide, an ammonium halide substituted with at least one C1 to C4 alkyl group), a transition metal salt and a lead salt. The transition metal salt can, for example, be selected from the group of salts of $Mn^{2+}$, $Mn^{3+}$, $Cu^{2+}$, $Ag^+$ $Cr^{3+}$, $Cr^{6+}$, $Fe^{2+}$ and $Fe^{3+}$. The lead salt can, for example, be a salt of $Pb^{2+}$. In several embodiments, the at least one inorganic additive is selected from the group of lithium bromide, lithium iodide, ammonium iodide, tetramethylammonium iodide, tetraethylammonium iodide, tetrapropylammonium iodide, tetrabutylammonium iodide, tetrabutylammonium bromide, manganese(II) chloride, manganese(II) sulphate and manganese(II) nitrate, chrom(III) chloride, alkali chromates, iron(II) chloride, iron(III) chloride, and lead(II) nitrate.

An electrochemical gas sensor in which the ionic liquid includes at least one inorganic additive can, for example, be used for the detection/measurement of $F_2$, $Cl_2$, $Br_2$, $I_2$, $O_3$, $ClO_2$, $NH_3$, $H_2$, HCl, HCN or a hydride gas.

In a number of such embodiments, the sensor is used for the detection/measurement of $Cl_2$, $Br_2$, $O_3$, $ClO_2$ or $NH_3$, and the ionic liquid electrolyte includes at least one inorganic additive selected from the group of an alkali halide, an ammonium halides, an ammonium halide substituted with at least one C1 to C4 alkyl group), a transition metal salt and a lead salt. Transition salts can, for example, be selected from the group of the salts of $Mn^{2+}$, $Mn^{3+}$, $Cu^{2+}$, $Ag^+$, $Cr^{3+}$ $Cr^{6+}$, $Fe^{2+}$ and $Fe^{3+}$. Lead salts can, for example, be a salt of $Pb^{2+}$. In several embodiments, the sensor is used for detection/measurement of $Cl_2$, $Br_2$, $O_3$, $ClO_2$ or $NH_3$, and the ionic liquid electrolyte includes at least one inorganic additive selected from the group of lithium bromide, lithium iodide, tetrabutylammonium iodide, tetrabutylammonium bromide, manganese(II) chloride, manganese(II) sulphate, manganese(II) nitrate, chrom(III) chloride, alkali chromates, iron(II) chloride, iron(III) chloride and lead(II) nitrate.

The addition of an alkali halide and/or an ammonium halide, such as, for example, LiI or NaBr, $NR_4I$ (wherein R is H, a methyl group, an ethyl group, a butyl group or combinations thereof), in small percentage proportions (for example, 0.05 to 15%) leads to a measurable increase in the sensitivity of the sensors to halogen gases and vapors. Higher alkali halides could, for example, be oxidized by $Cl_2$. The following sensor reaction is possible:

Partial reaction of analyte:
with additive: $Cl_2 + 2\ Br^- \rightarrow Br_2 + 2\ Cl^-$
Sensor reaction: $Br_2 + 2e^- \rightarrow 2\ Br^-$ That the sensor reactions are secondary reactions of the salts in the electrolyte is evidenced by the observation that reactions also take place when there is no active catalyst for the transformation of the analyte gases, but only a carbon conduction. The same results (increase of sensitivity and high selectivity) are observed in the case of, for example, ammonia sensors when adding manganese and copper salts. Transition metals might also build complexes (such as copper tetramine) with the analyte gases and cause a sensor signal by shifting the potential.

A significant advantage in the use of inorganic additives is the selectivity of the sensor, as it offers the possibility for the target or analyte gas to generate a specific detection reaction. Using a combination of various additives, cross-sensitivity patterns can be created, which would not be possible in classic (aqueous) electrolyte sensor systems or in systems using pure ionic liquids as electrolytes.

Ionic liquids with at least one inorganic additive function as ionic conductors in gas sensors in the classic sense of a Clark cell, as described above. Noble metal catalysts or carbon can, for example, be used as electrocatalysts in a sensing electrode and a counter electrode in a two electrode system, or with an additional reference electrode in a three-electrode system (or with additional electrodes if the sensor is, for example, equipped with a protective electrode or additional sensing electrodes). Inorganic additives can be added to the ionic liquids in the form of an aqueous solution or melted together with the ionic liquids. The manner of addition depends on the water solubility of the additive, on the hydrophilicity of the ionic liquid and on any secondary reactions.

In the case of the addition of at least one inorganic additive to the base electrolyte of a representative $Cl_2$ sensor, it was observed that all sensors including additives (see FIG. 5) reacted more sensitively to the analyte or target gas than sensors of identical construction without additives (see also, Table 2, which sets forth data for a gold/carbon (70:30) electrode).

Furthermore, increased consistency is observed between the sensors. When comparing the sensitivity distribution of sensors with and without inorganic additives, it is observed that chlorine sensors with LiBr exhibit a significantly smaller scattering. This is demonstrated in comparing the average values of the standard deviation of both sensor types (see FIG. 6).

TABLE 2

| to Cl2 | Potentials [mV] SE vs RE | S [nA/ppm] |
|---|---|---|
| EMIM MeSO₃ | −93 | 1800 |
| EMIM MeSO₃ + LiBr | −130 | 2000 |
| EMIM MeSO₃ + TBAI | −56 | 2460 |
| EMIM MeSO₃ + LiI | −5 | 2260 |

Considering the potential differences measured between the sensing and the reference electrode, neither a correlation to sensor sensitivities nor to sensor stability can be detected.

However, if one replaces the gold/carbon electrode with an electrode made of pure carbon, the sensors still function to detect chlorine gas. This result is an indication that the reaction to chlorine includes a secondary reaction of the electrolyte with the chlorine gas and not only a reaction of the chlorine gas with the catalyst of the sensing electrode. Addition of LiCl as an additive does not lead to any significant sensing signal. Specific inorganic additive or additives can be selected to achieve the desired sensing effects.

FIG. 1A illustrates a gas sensor 1 used in several studies which includes a sensor housing 2. A sensing or working electrode 3, a reference electrode 5, and a counter electrode 6 are positioned within sensor 1 in such a manner that the sensing electrode 3 is in fluid connection with the external atmosphere via a gas permeable membrane. The electrodes are ionically connected with one another via a separator 4 fabricated from glass fibers or silicate structures which are impregnated with an electrolyte as described above. A reserve volume 7 provides volume so that water can be absorbed without electrolyte leakage in the case of a hydroscopic electrolyte. Sensor 1 is connected with sensing electronics 8 which amplifies the sensor current to a sensing signal if an analyte or target gas is present.

Figure 1B:
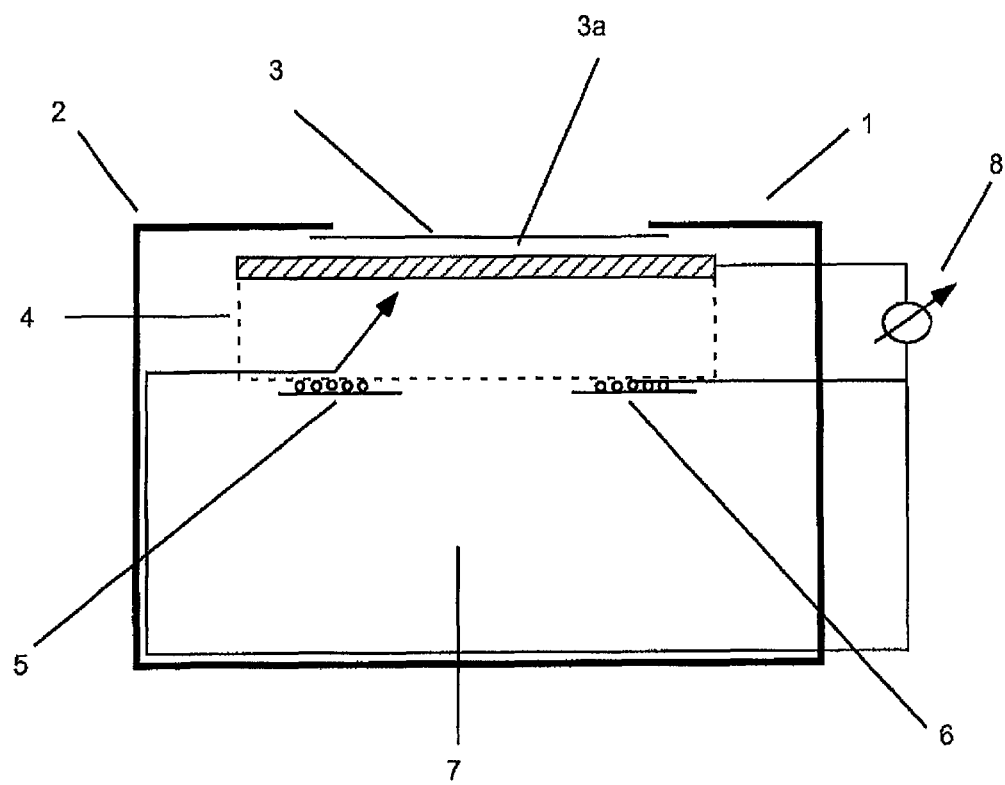
FIG. 1B illustrates a schematic representation of an embodiment of an electrochemical, three-electrode gas sensor including a quasi-solid electrolyte.

FIG. 1B illustrates another gas sensor 1 used in several studies which includes a sensor housing 2, in which a working electrode 3a, a reference electrode 5, and a counter electrode 6 are positioned so that working electrode 3a is in fluid connection with the ambient atmosphere via gas permeable membrane 3. Working electrode 3a includes a layer of catalyst/electrode material and electrolyte (for example, an ionic liquid with additive), which is absorbed in a powdered solid material based on $SiO_2$. The electrodes are electrically interconnected via a separator 4 formed of glass fibers or silicate structures, which are saturated with the electrolyte. As described above, an additive or additives can be immobilized upon separator 4 or one or more other solid supports that can, for example, be positioned in the vicinity of the catalyst of working electrode 3a. An additive or additives can also or alternatively be immobilized upon working electrode 3a and/or upon another electrode. Reference electrode 5 and counter electrode 6 are positioned side by side on the side of separator 4 that is opposite working electrode 3a. A compensating or reserve volume 7 provides volume for water to be absorbed in the case a hygroscopic electrolyte. Sensor 1 is connected to electronic measuring equipment 8, which maintains a stable potential difference between working electrode 3a and reference electrode 6 and amplifies sensor current to provide a measuring signal in the presence of analyte gas.

Figure 1C:
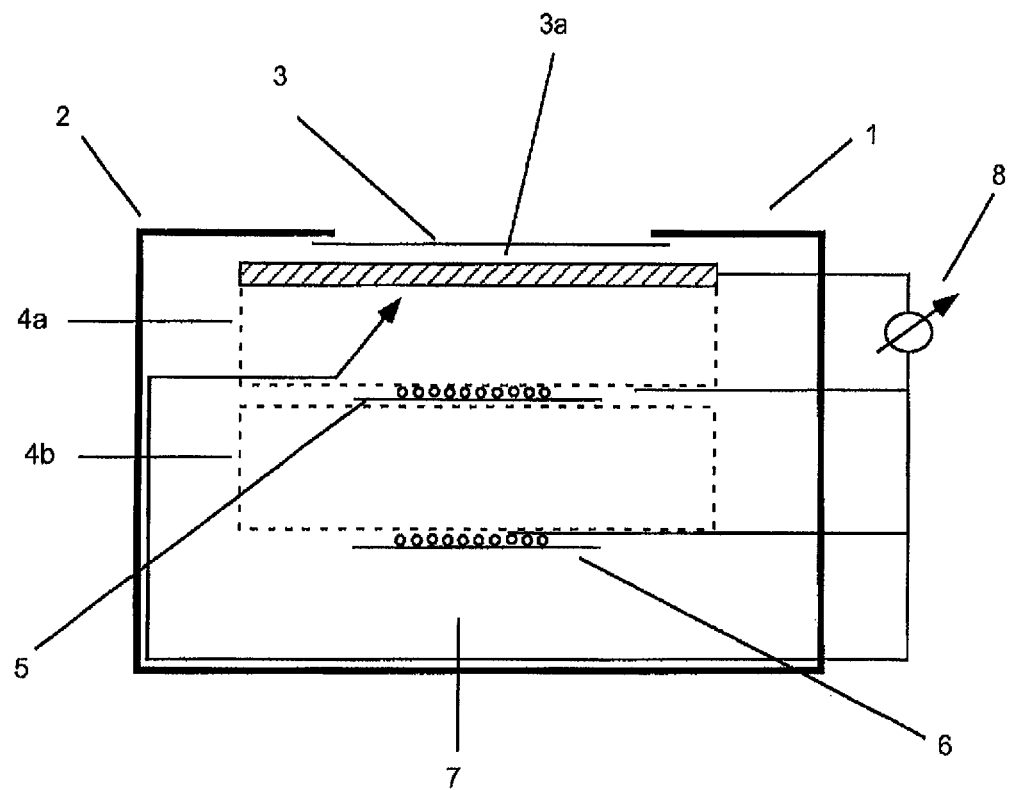
FIG. 1C illustrates a schematic representation of another embodiment of an electrochemical, three-electrode gas sensor including a quasi-solid electrolyte.

FIG. 1C illustrates another embodiment of a gas sensor 1 including a sensor housing 2, in which working electrode 3a, reference electrode 5, and counter electrode 6 are positioned so that working electrode 3a is in fluid connection with the ambient atmosphere via a gas permeable membrane 3 as described above. Working electrode 3a includes a layer of catalyst/electrode material and electrolyte (for example, an ionic liquid with additive), which is absorbed in a powdered solid material based on $SiO_2$. Working electrode 3a and reference electrode 5 are electrically interconnected via a separator 4a formed from glass fibers or silicate structures, which are saturated with the electrolyte. Counter electrode 6 is in electrical connection with reference electrode 5 and working electrode 3a via a second separator 4b positioned between reference electrode 5 and counter electrode 6. Counter electrode 6 is located on the side of separator 4b opposite reference electrode 5. As described above, compensating volume 7 provides volume for water to be absorbed in case of a hydroscopic electrolyte. Once again, sensor 1 is connected to electronic measuring equipment 8, which maintains a stable potential difference between working electrode 3a and reference electrode 5 and amplifies sensor current to provide a measuring signal in the presence of analyte gas.

As described above, FIG. 2 illustrates the performance difference between sensors with and without an additive in the ionic liquid electrolyte. Signal stabilization was effected by the addition of uric acid to the electrolyte. The comparison between a pure ionic liquid (1-ethyl-3-methylimidazolium methanesulphonate) and the same ionic liquid with uric acid additive in the case of gas exposure with 4 ppm chlorine is illustrated.

Figure 3:
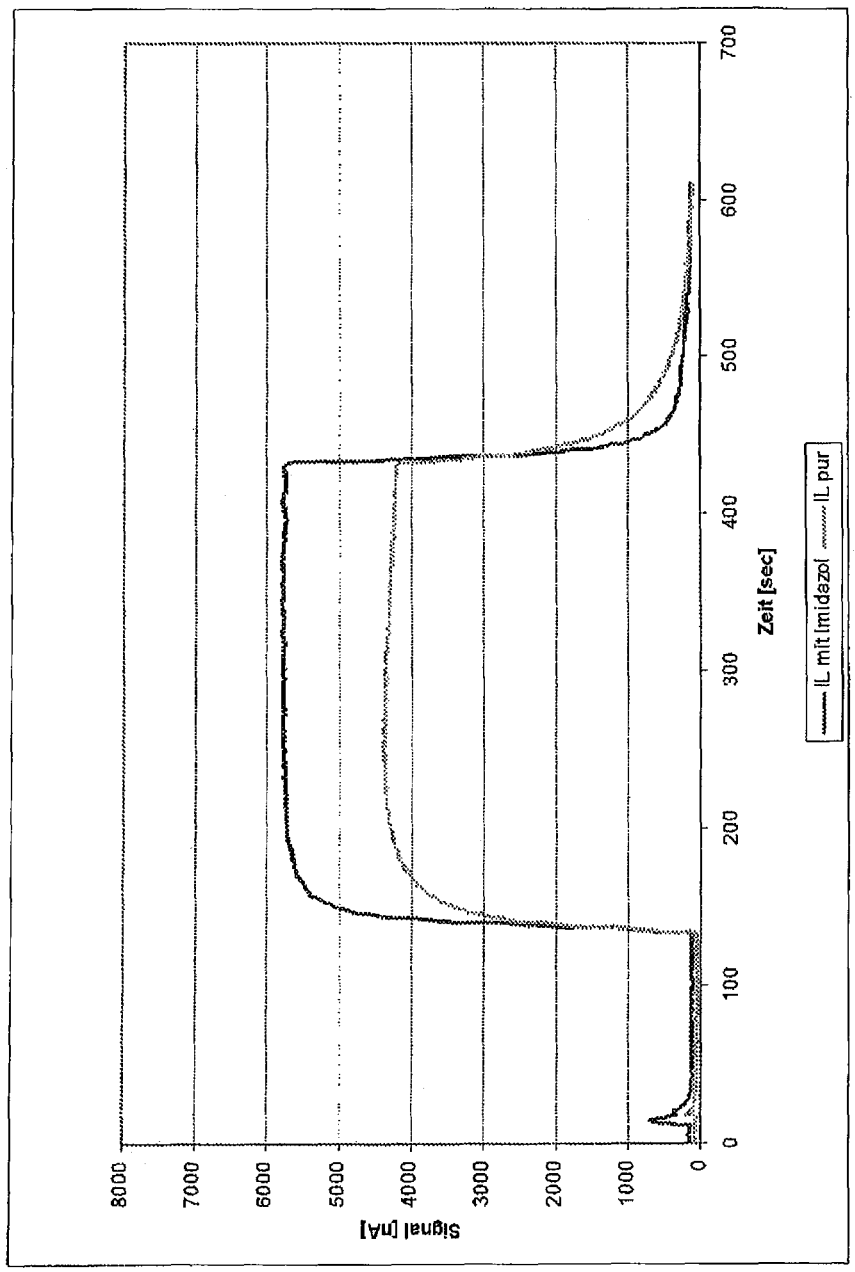
FIG. 3 illustrates a graph of a comparison of sensor performance (signal versus time) between sensors including an ionic liquid electrolyte with imidazole as an additive to the electrolyte and without an additive, respectively.

FIG. 3 illustrates a comparison of sensor performance with imidazole as an additive to the electrolyte (1-ethyl-3-methylimidazolium methanesulphonate) and without an additive. An increase in sensor sensitivity and sensor stability is observed with use of imadazole as an additive. The sensors were exposed to 10 ppm $SO_2$ gas.

Figure 4:
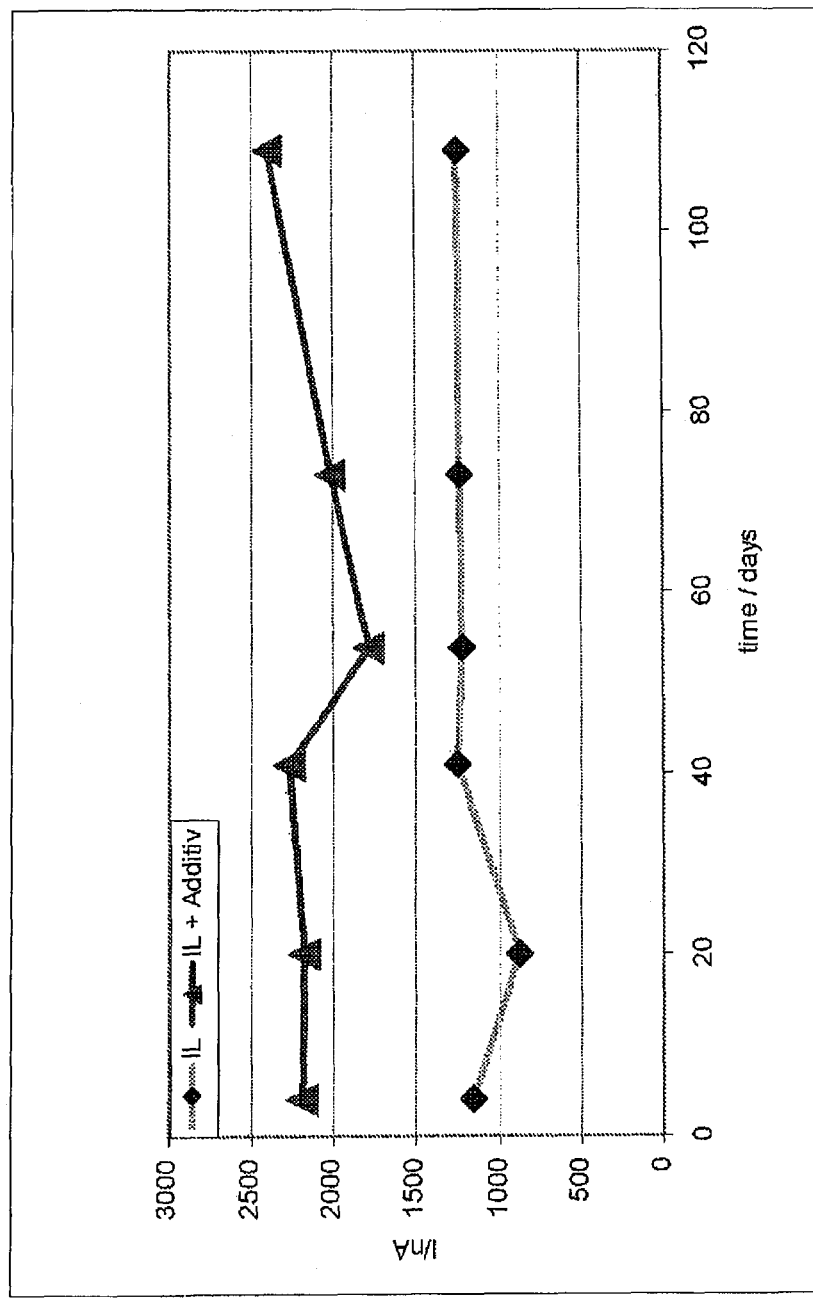
FIG. 4 illustrates a graph of long-term monitoring of sensors including an ionic liquid electrolyte with and without an imidazole additive.

FIG. 4 illustrates the results of studies in which sensors including an ionic liquid electrolyte with an imidazole additive and sensors including an ionic liquid electrolyte without an additive were monitored over a sustained period of time. The group of sensors with imidazole as an additive were more sensitive during a maturation period (that is, the first two weeks) than the control group of sensors without additive. The increased sensitivity of the sensors including the additive was observed throughout the monitoring period. Furthermore, the sensor curves were stable during the monitoring period (that is, the sensor curves did not collapse during the long-term gas exposure).

Figure 5:
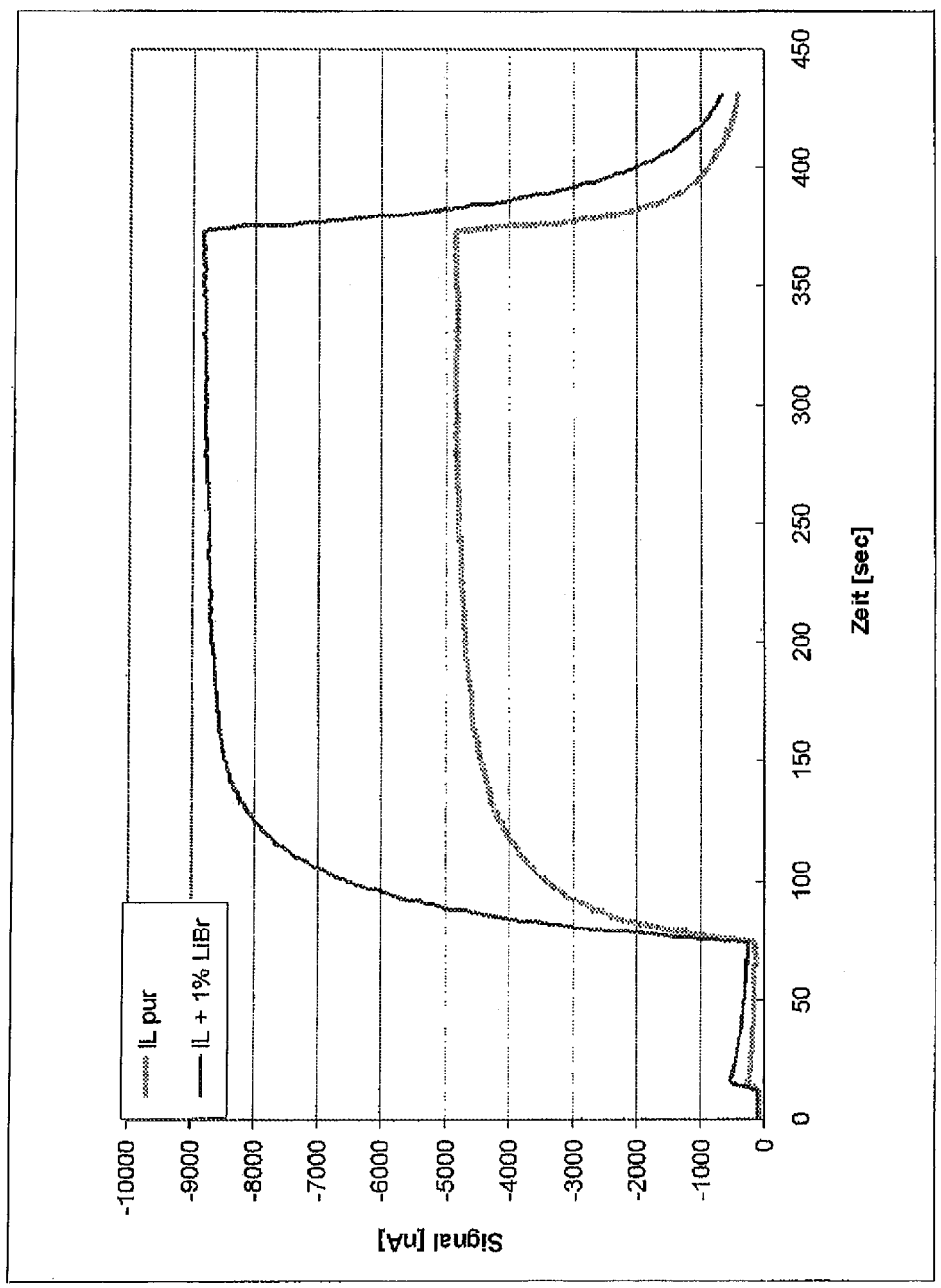
FIG. 5 illustrates a graph of performance difference between the sensors including an ionic liquid electrolyte with and without an inorganic additive.

FIG. 5 illustrates the performance difference between sensors with and without inorganic additive. Sensors with LiBr as an additive are more sensitive to the chlorine gas, and the signals of individual sensors vary less than sensors including the same ionic liquid electrolyte without an additive The ionic liquid in the studies of FIG. 5 was 1-ethyl-3-methylimidaolium methanesulphonate). The sensors were exposed to 4 ppm chlorine gas.

Figure 6:
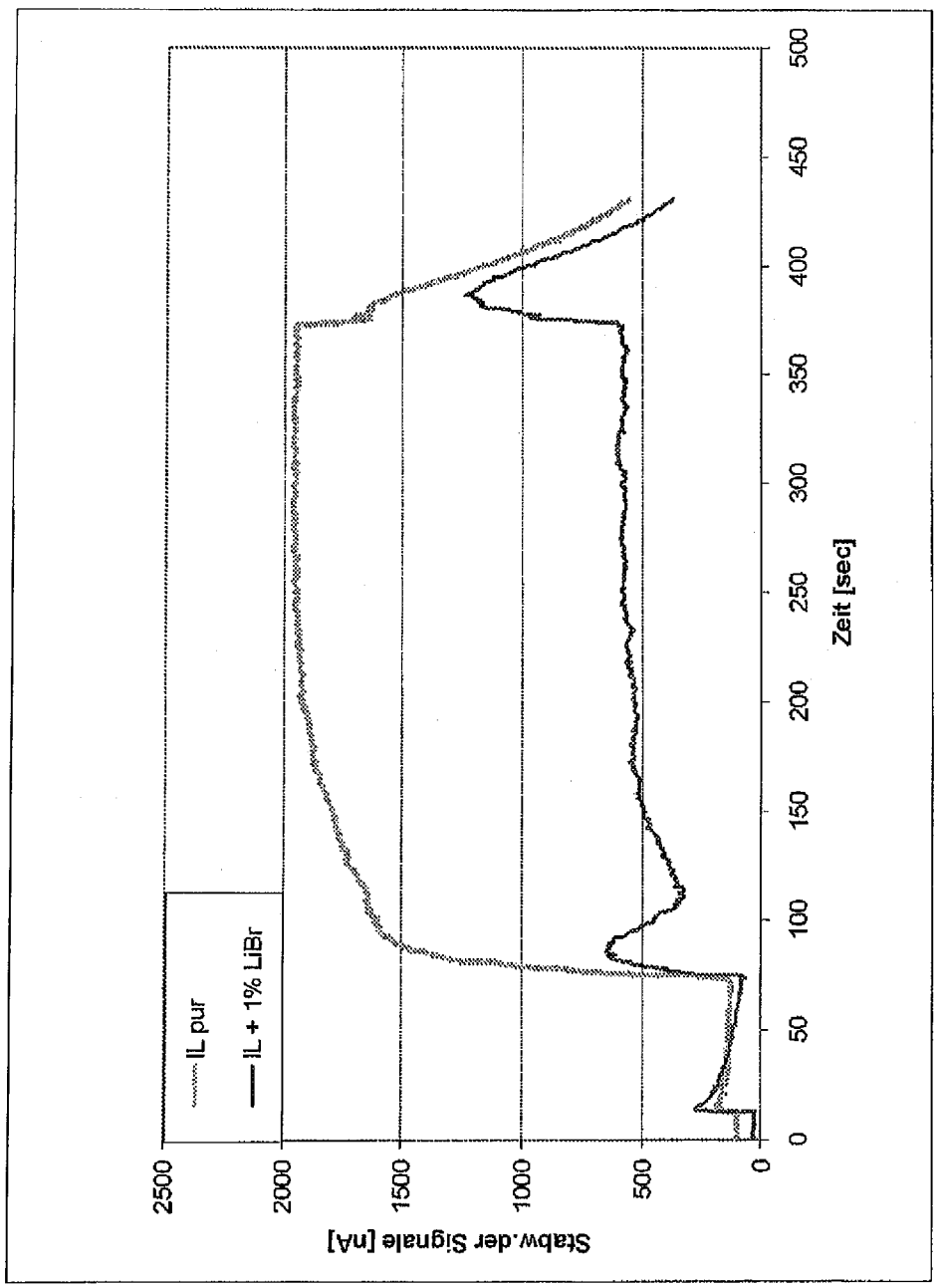
FIG. 6 illustrates a graph of a comparison of standard deviation of sensors including an ionic liquid electrolyte with and without an inorganic additive.

FIG. 6 illustrates a comparison of standard deviation of the signal for sensors with and without an inorganic additive (LiBr) during the detection of chlorine (4 ppm chlorine gas). The sensitivities of the sensors including the additive fall within a significantly narrower range than the sensitivities of sensors without an additive.

Figure 7:
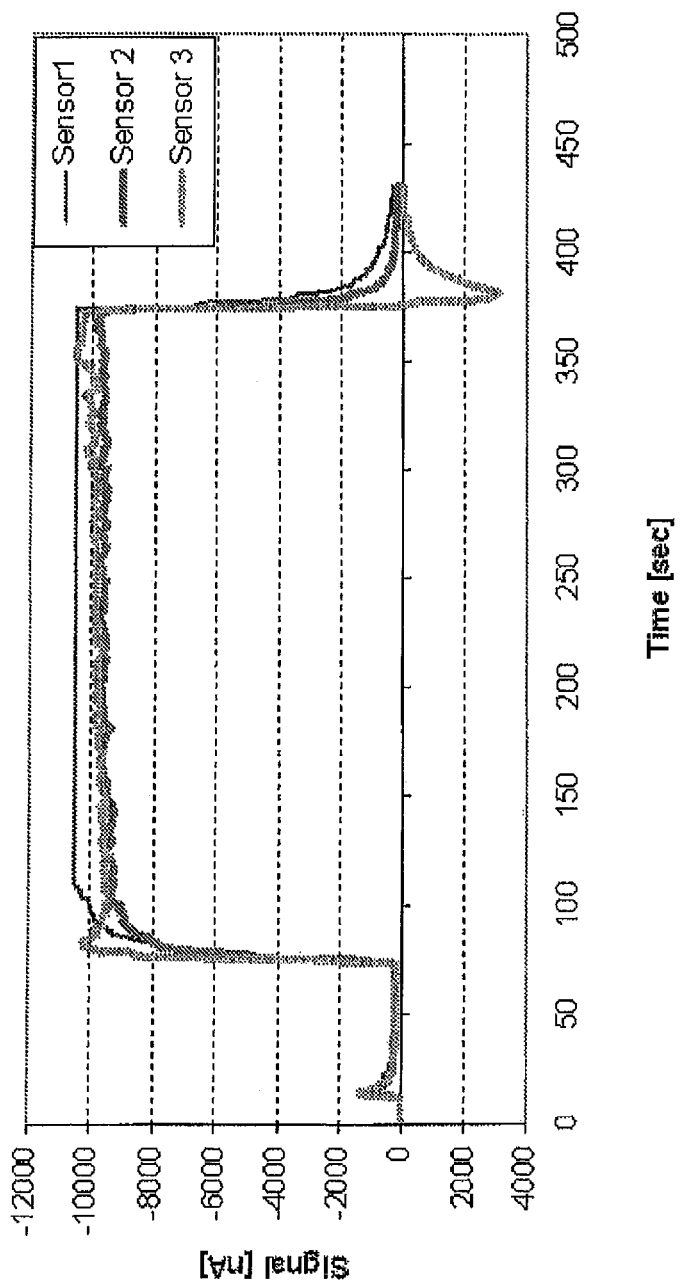
FIG. 7 illustrates a graph of sensor performance of a chlorine sensor including a quasi-solid ionic liquid electrolyte, which includes imidazole and LiBr as additives, upon exposure to 4 ppm of chlorine gas.

FIG. 7 illustrates a comparison of the performance of sensors with an electrolyte including lithium bromide and imidazole additives, resulting in signal stabilization (as compared to an electrolyte without such additives). In forming the electrolyte, 1-ethyl-3-methylimidazolium methanesulfonate (EMIM MeSO3) was mixed with 5% of lithium bromide and 1% of imidazole, respectively, in a ratio of 1:2. Subsequently, the mixture was mixed with a silica gel in a ratio of 2:1. The resultant powder was then pressed into disks having a thickness of approximately 1 mm. The sensors were exposed to 4 ppm of $Cl_2$ in air with a flow rate of 200 l/h. The sensors exhibited a short response time and high sensitivity to chlorine. Little signal variation between different sensors and an excellent signal-to-noise ratio were observed.

Figure 8:
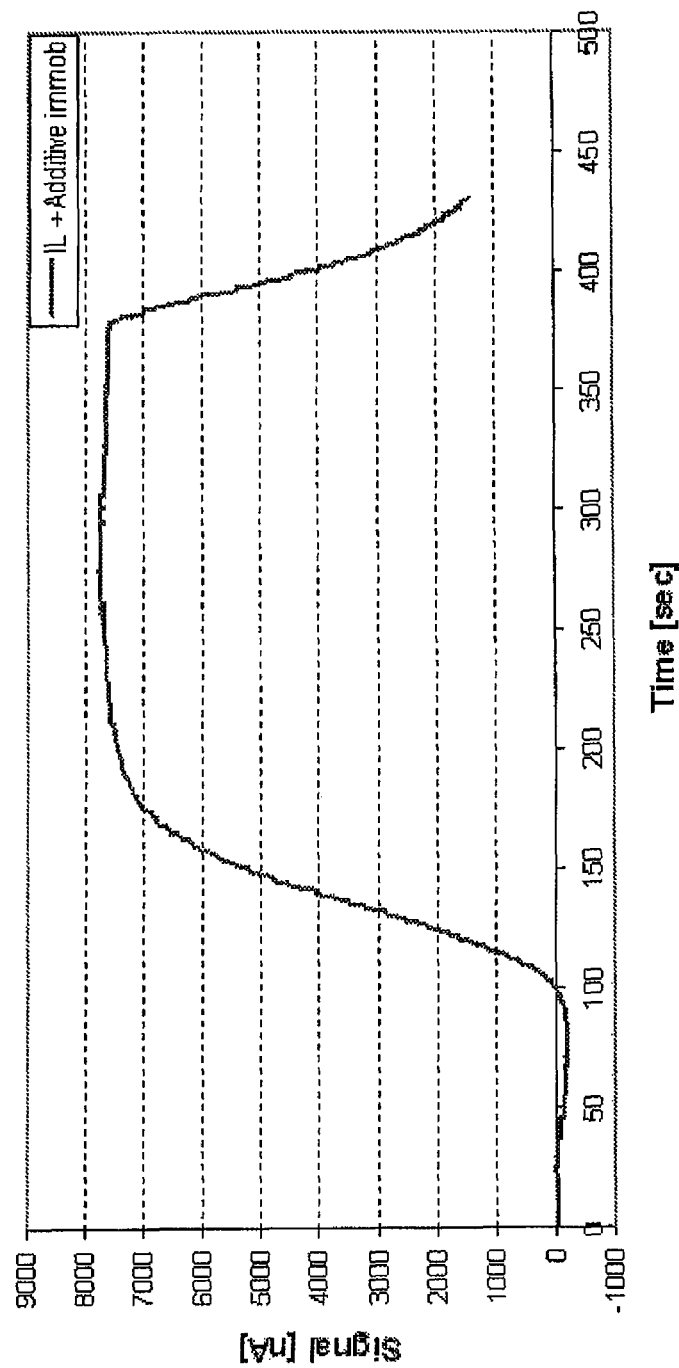
FIG. 8 illustrates a graph of sensor performance of an $NH_3$ sensor including 1% of $MnCl_2$ as an additive to an ionic liquid electrolyte absorbed within a silica gel.

FIG. 8 illustrates the performance of an $NH_3$ sensor having an electrolyte including EMIM MeSO3 with 1% of $MnCl_2$ as an additive. The liquid electrolyte was absorbed on silica gel. The sensor was exposed to 50 ppm of $NH_3$ in air with a flow rate of 200 l/h.

EXAMPLES

Example 1—$Cl_2$ Sensor

The sensor assembly included a sensing electrode (SE) including a mixture of gold (Au) and carbon (C) (30:70), a counter electrode (CE) formed with platinum and a reference electrode (RE) formed with platinum (see FIG. 1A). The electrodes were applied to a gas-permeable PTFE-membrane in each case. Electrolyte-impregnated separators made from glass-fiber material were located between the electrodes to ensure ionic conductivity between the electrodes and to prevent short circuits between the electrodes. The sensor can also functions if the RE and CE are not arranged parallel as illustrated in FIG. 1A, but rather in series or above one another.

The electrolyte included the ionic liquid 1-ethyl-3-methylimidazolium methanesulphonate (EMIM $MeSO_3$) with one percent by weight of uric acid as an additive. The additive was added in solid form to the EMIM $MESO_3$ which had been heated to 100° C. A clear solution was produced.

The sensor was exposed to 4 ppm $Cl_2$ in air at a flow of 200 l/h.

Figure 2:
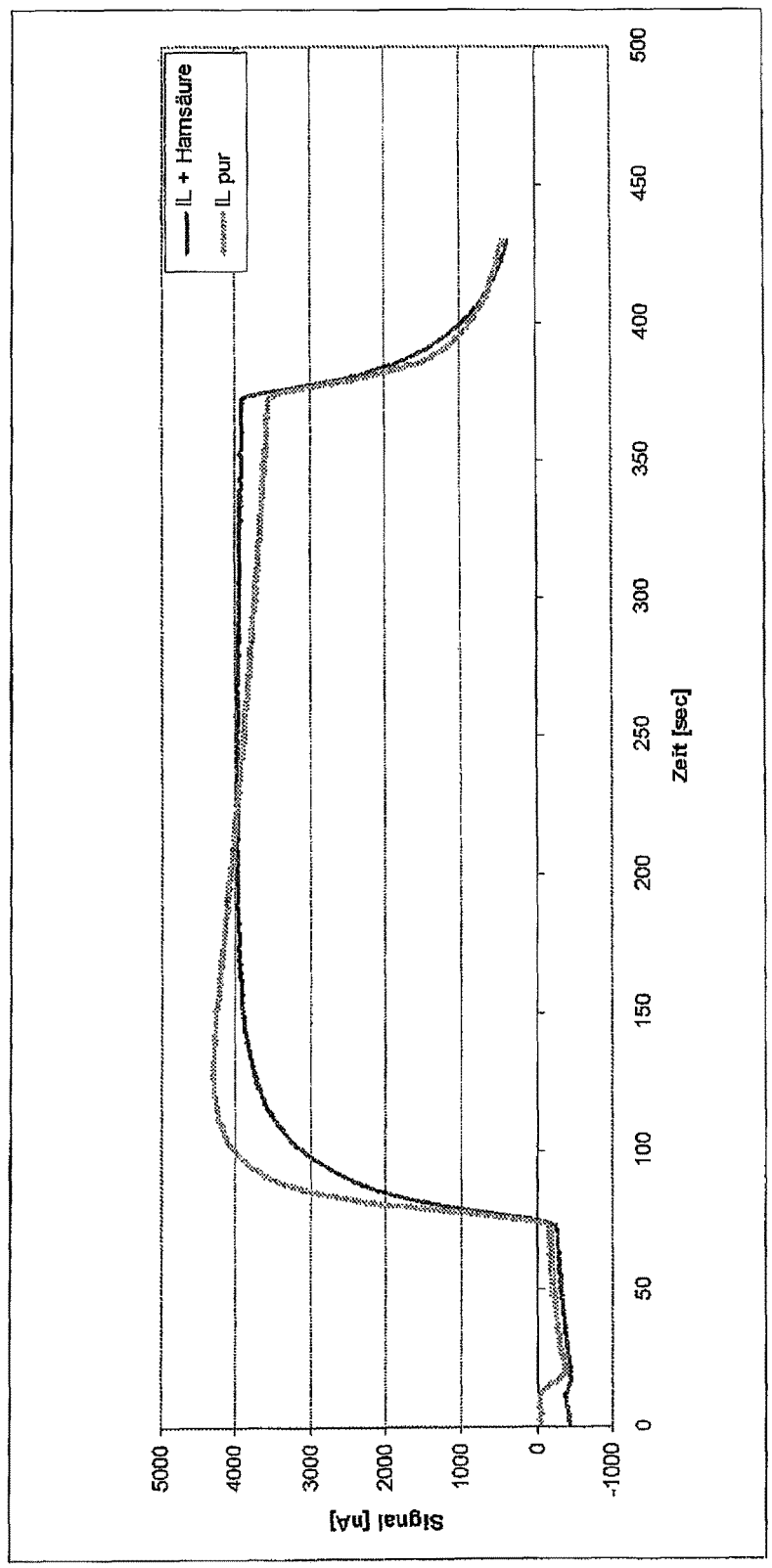
FIG. 2 illustrates a graph of performance difference (signal versus time) between sensors including an ionic liquid electrolyte with and without an organic additive.

The results are illustrated graphically in FIG. 2.

Example 2—$SO_2$ Sensor

The sensor was assembled in a manner similar to that of Example 1. The ionic liquid of the electrolyte was EMIM $MeSO_3$ and included 1% imidazole as an additive (rather that uric acid, as in Example 1). Sensors wherein the SE was formed from an Au/Pd alloy or from Pt functioned very reliably. The sensor was exposed to 10 ppm $SO_2$ gas in air at a flow of 200 l/h. The result are illustrated graphically in FIG. 3.

Example 3—$Cl_2$ Sensor

The sensor was assembled in a manner similar to that of Example 1. The ionic liquid of the electrolyte was EMIM $MeSO_3$ and included 10% LiBr, which was stirred, in a crystalline state, into the ionic liquid which had been heated to 100° C. until a clear solution was obtained. The SE was formed from pure carbon. The sensor was exposed to 4 ppm $Cl_2$ in air at a flow of 200 l/h. The results are illustrated graphically in FIGS. 4 and 5.

Example 4—$Cl_2$ Sensor (Quasi-Solid Electrolyte)

The general design of the electrochemical sensors studied is set forth in the schematic illustration of FIG. 1B. The working electrode (WE) included a mixture of gold (Au) and carbon (C). The counter electrode (CE) and reference electrode (RE) each included platinum (Pt). Each of the electrodes was applied to a gas permeable PTFE membrane. Separators of silica gel, which were saturated with electrolyte, were positioned between the electrodes to provide ionic conductivity between the electrodes, while preventing short circuits between the electrodes. The sensors also functions if the RE and the CE are arranged as illustrated in FIG. 1C. The electrolyte included 1-ethyl-3-methylimidazolium methanesulfonate (EMIM $MeSO_3$) with one percent by weight of each of imidazole and lithium bromide as additives. Each additive was added in solid form to EMIM $MeSO_3$, which was heated to 100° C. A clear solution was formed. The solution was mixed with silica gel in a ratio of 1:2. The resultant powder was pressed into disks having a thickness of 1 mm in a tablet press. The sensors were exposed to 4 ppm of $Cl_2$ in air with a flow rate of 200 l/h. The results of the studies are set forth in FIG. 7.

Example 5—$SO_2$ Sensor (Quasi-Solid Electrolyte)

The general design of the sensor was similar to the sensor of Example 4. Unlike the sensors of Example 4, the working electrode was not applied to a membrane. The catalyst material and the electrolyte powder were directly compressed into an electrode, which was covered by a PTFE membrane. The sensor was exposed to 10 ppm of $SO_2$ gas in air with a flow rate of 200 l/h.

Example 6—$NH_3$ Sensor

The general design of the sensor was similar to Example 4. Unlike the sensors of Example 4, the electrolyte was EMIM MeSO3 including 1% of $MnCl_2$ additive. The additive was stirred in crystalline form in the ionic liquid, which was heated to 100° C., until a clear solution was obtained. The solution was mixed with silica gel in a ratio of 1:2. The resultant powder was pressed into disks having a thickness of 1 mm in a tablet press. The sensor functions in the case of a WE including a mixture of gold and carbon, as well as a WE including pure carbon. The sensor was exposed to 50 ppm of $NH_3$ in air with a flow rate of 200 l/h. Results of the studies are set forth in FIG. 8.

The foregoing description and accompanying drawings set forth representative embodiments. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. An electrochemical gas sensor, comprising an electrolyte comprising at least one ionic liquid, wherein the ionic liquid comprises an additive portion comprising at least one organometallic additive,
    wherein the at least one organometallic additive is selected from the group comprising organometallic porphyrins and organometallic porphyrin derivatives.

2. The electrochemical gas sensor according to claim 1, wherein the sensor comprises at least two electrodes in electrical contact with the ionic liquid, the electrodes being separated from one another by a separator or by space.

3. The electrochemical gas sensor according to claim 2, wherein the electrodes comprise independently, the same or different, a metal selected from the group comprising Cu, Ni, Ti, Pt, Ir, Au, Pd, Ag, Ru, Rh, an oxide of Cu, Ni, Ti, Pt, Ir, Au, Pd, Ag, Ru, or Rh, mixtures thereof, or carbon.

4. The electrochemical gas sensor according to claim 1, wherein organometallic additives are present in an amount of 0.05 to 5 weight-%.

5. The electrochemical gas sensor according to claim 1, wherein the ionic liquid comprises at least one cation which is selected from the group comprising imidazolium, pyridinium, and guanidinium, the cation being unsubstituted or substituted with at least one of an aryl group or a C1 to C4 alkyl group, the aryl group and the C1 to C4 alkyl group being unsubstituted or substituted with at least one of a halogen, a C1 to C4 alkyl group, a hydroxyl group or an amino group.

6. The electrochemical gas sensor according to claim 1, wherein the ionic liquid comprises at least one anion selected from the group comprising a halide anion, a nitrate anion, a nitrite anion, a tetrafluoroborate anion, a hexafluorophosphate anion, a polyfluoroalkane sulphonate anion, a bis(trifluoromethylsulfonyl)imide anion, an alkyl sulphate anion, an alkane sulphonate anion, an acetate anion, and an anion of a fluoroalkane acid.

7. The electrochemical gas sensor according to claim 1, wherein the ionic liquid comprises at least one anion selected from the group comprising a C1-C6 alkyl sulphate anion and a C1-C6 alkane sulphonate anion.

8. The electrochemical gas sensor according to claim 1, wherein the ionic liquid comprises 1-ethyl-3-methylimidazolium methanesulphonate.

9. The electrochemical gas sensor according to claim 1, wherein the electrolyte is substantially absorbed in a solid material.

10. The electrochemical gas sensor according to claim 1, wherein at least a part of the organometallic additive portion is immobilized upon a solid support, is immobilized upon the solid material, or is immobilized upon at least one of the electrodes.

11. Use of an electrochemical gas sensor according to claim 1 for the detection/measurement of gases selected from the group comprising CO, $O_2$, NO, $NO_2$ and $H_2$.

12. An electrochemical gas sensor, comprising a housing comprising at least one inlet, at least two electrodes in the housing, an electrolyte in contact with the at least two electrodes, wherein the electrolyte comprises an ionically conductive liquid and an additive portion comprising at least one organometallic additive and the electrolyte is substantially absorbed in a solid material,
    wherein the at least one organometallic additive is selected from the group comprising organometallic porphyrins and organometallic porphyrin derivatives.

13. The electrochemical gas sensor according to claim 12, wherein the solid material comprises a powdered silicate having an average particle size of at least 5 µm, a specific surface area of at least 50 $m^2$/g, and a $SiO_2$ content of at least 95% by weight.

14. The electrochemical gas sensor according to claim 12, wherein the solid material is a fibrous nonwoven glass fiber, the solid material is present in the sensor as a bed, in a layered arrangement or in compressed form, or the solid material is present in the sensor in compressed form with the at least two electrodes pressed therein.

15. The electrochemical gas sensor according to claim 5, wherein the amino group comprises an imidazolium cation.

16. The electrochemical gas sensor according to claim 7, wherein the ionic liquid comprises at least one anion selected from the group comprising a metal sulphate anion, an ethyl sulphate anion, a butyl sulphate anion, a methanesulphonate anion, an ethanesulphonate anion, and a butanesulphonate anion.

17. The electrochemical gas sensor according to claim 1, wherein the at least one organometallic additive is selected from the group of prophyrins with at least one meso-alkyl substituent, at least one β-alkyl substituent, at least one aryl substituent, and their derivatives.

18. The electrochemical gas sensor according to claim 1, wherein the organometallic porphyrin is a metal phthalocyanine with $Mn^{2+}$, $Cu^{2+}$, $Fe^{2+/3+}$ or $Pb^{2+}$ as the metal cation.

19. The electrochemical gas sensor according to claim 13, wherein the solid material comprises a powdered silicate having an average particle size of 100 µm, a specific surface area of 190 $m^2$/g, and a $SiO_2$ content of at least 98% by weight.

* * * * *

UNITED STATES PATENT AND TRADEMARK OFFICE
CERTIFICATE OF CORRECTION

PATENT NO. : 9,945,806 B2
APPLICATION NO. : 14/743045
DATED : April 17, 2018
INVENTOR(S) : Rolf Eckhardt et al.

It is certified that error appears in the above-identified patent and that said Letters Patent is hereby corrected as shown below:

On the Title Page

Column 1, after Item (63), insert:
-- (30) Foreign Application Priority Data
Dec. 1, 2008 (DE) ..........................................10 2008 044 239.9
Dec. 1, 2008 (DE) ..........................................10 2008 044 238.0 --

In the Claims

Column 18, Line 52, Claim 17, delete "prophyrins" and insert -- porphyrins --

Signed and Sealed this
Seventeenth Day of July, 2018

Andrei Iancu
*Director of the United States Patent and Trademark Office*